(12) United States Patent
Cote et al.

(10) Patent No.: US 6,250,502 B1
(45) Date of Patent: Jun. 26, 2001

(54) PRECISION DISPENSING PUMP AND METHOD OF DISPENSING

(76) Inventors: Daniel A. Cote, 522 Estey La., Windsor, VT (US) 05089; Christopher A. Hofmeister, P.O. Box 502, 172 Mills Shore Dr., Hampstead, NH (US) 03841; Jayanth Prabharkar, 281 New Boston Rd., Bedford, NH (US) 03110

( * ) Notice: Subject to any disclaimer, the term of this patent is extended or adjusted under 35 U.S.C. 154(b) by 0 days.

(21) Appl. No.: 09/398,683

(22) Filed: Sep. 20, 1999

(51) Int. Cl.[7] ............................... B67D 5/40; F04B 9/08
(52) U.S. Cl. ........................ 222/1; 222/380; 417/383
(58) Field of Search .................... 222/1, 380, 334; 417/383, 389

(56) References Cited

U.S. PATENT DOCUMENTS

| | | | |
|---|---|---|---|
| 2,514,882 | * 7/1950 | Leiman | 417/383 |
| 3,220,608 | * 11/1965 | Porter, Jr. | 222/380 |
| 4,068,982 | * 1/1978 | Quarve | 417/383 |
| 4,950,134 | 8/1990 | Bailey et al. | 417/383 |
| 5,167,837 | 12/1992 | Snodgrass et al. | 210/767 |
| 5,262,068 | 11/1993 | Bowers et al. | 210/767 |
| 5,819,983 | 10/1998 | White et al. | 222/1 |

* cited by examiner

Primary Examiner—Lesley D. Morris
(74) Attorney, Agent, or Firm—Christopher Hofmeister

(57) ABSTRACT

A precision dispensing pump for dispensing fluids and method of dispensing for use in semiconductor packaging and/or semiconductor assembly. The precision dispensing pump employs a working fluid displacement drive for volumetric displacement of a working fluid, a dispensing reservoir for containment of dispensing fluid and a isolation diaphragm for isolating the working fluid from dispensing fluid in the dispensing reservoir. Volumetric displacement of dispensing fluid in the dispensing reservoir is proportional to volumetric displacement of working fluid in the working fluid displacement drive.

26 Claims, 7 Drawing Sheets

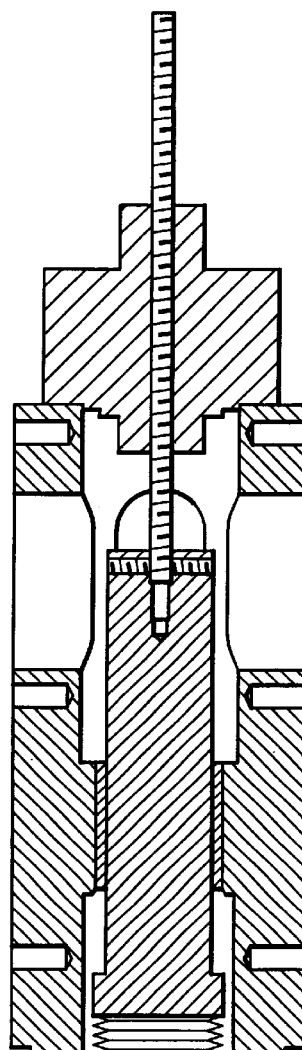
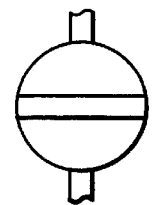
FIG.5
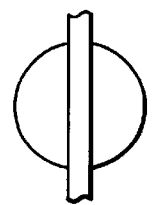
FIG.6
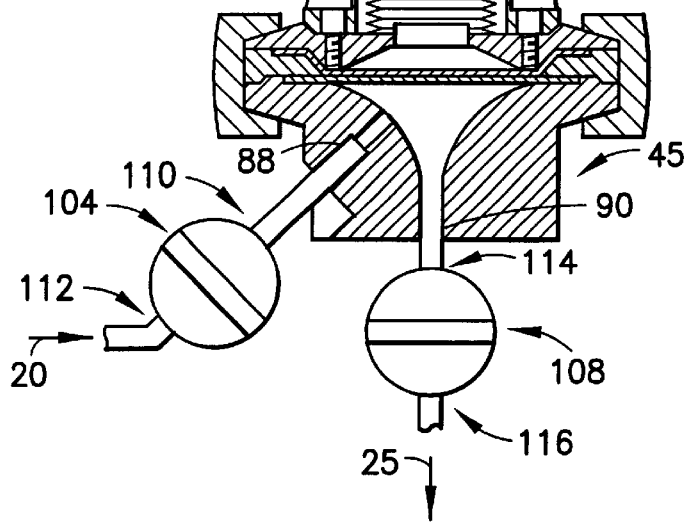
FIG.4

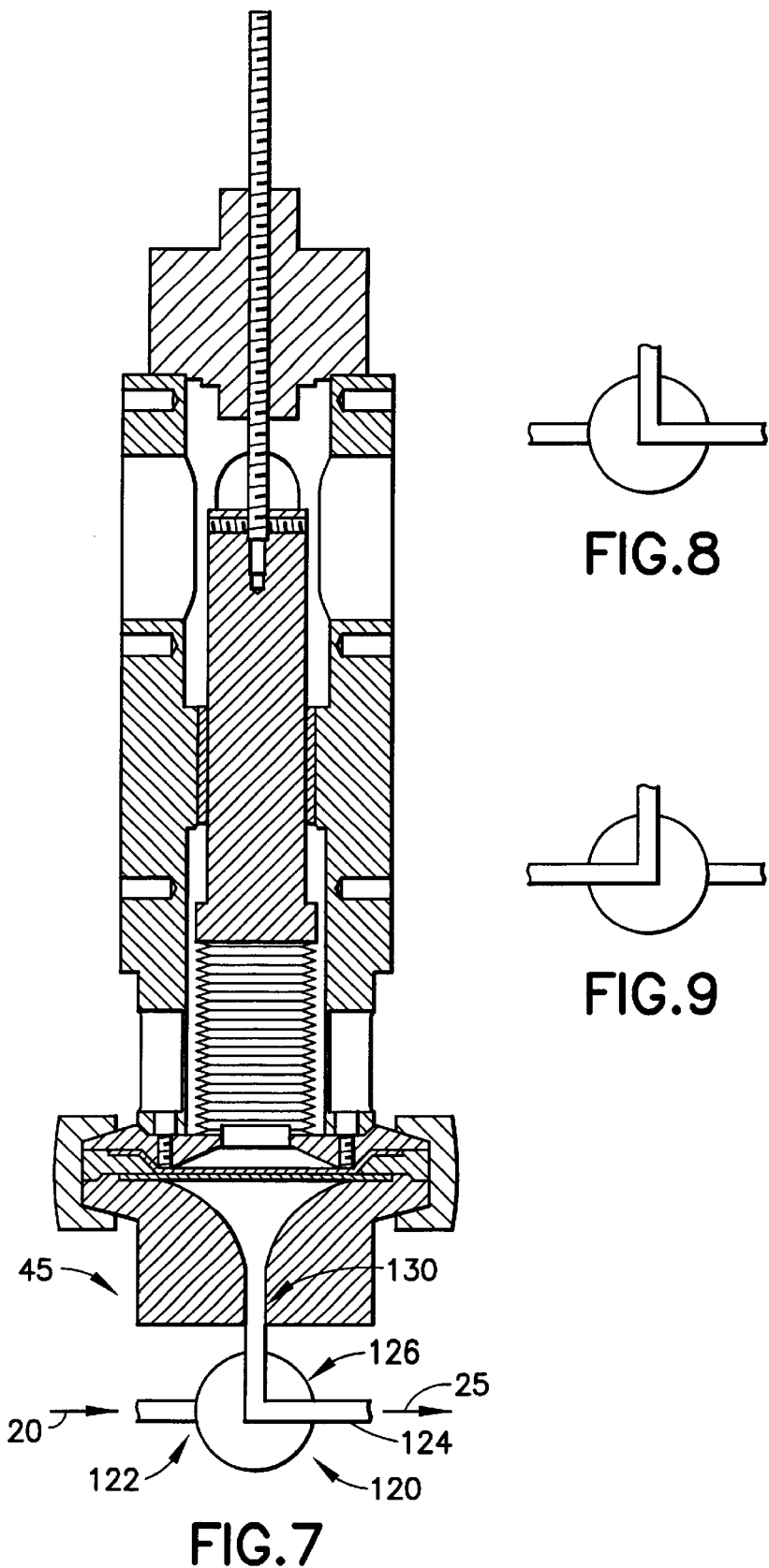

PRECISION DISPENSING PUMP AND METHOD OF DISPENSING

BACKGROUND OF THE INVENTION

It is well known to use pumps for dispensing of adhesives, encapsulates, pastes and other high through low viscosity liquids and pastes. Recent developments in the processing of semiconductors include the introduction of packaging techniques which require high speed precision dispensing of epoxies, solder pastes encapsulates and underfill materials. In the past, augering screw type pumps like those disclosed in U.S. Pat. Nos. 5,819,983 and 5,795,390 have been employed in such applications; however with the advent of higher precision dispensing requirements, these pumps have reached their limit in terms of performance and accuracy. In order to overcome accuracy limitations of augering screw type pumps, a series of piston based positive displacement pumps like those manufactured by Asymtek, a Nordson Company have evolved. While exceeding accuracy of augering screw type pumps, these piston based pumps have suffered limitations in terms of the ability to service and clean parts of the pump exposed to the various fluids.

The apparatus of the present invention relates generally to positive displacement pumps. The invention further relates to positive displacement pumps for dispensing of adhesives, encapsulates, pastes and other high through low viscosity liquids and pastes.

One object of the present invention is to provide a precision dispensing pump for high accuracy dispensing of liquids such as adhesives, encapsulates, pastes and other high through low viscosity liquids and pastes.

Another object of the present invention is to provide a positive displacement pump for high accuracy dispensing of liquids such as adhesives, encapsulates, pastes and other high through low viscosity liquids and pastes.

Another object of the present invention is to provide a precision dispensing pump which has simplified cleaning of parts exposed to dispensing fluids in order to minimize down time for service.

Another object of the present invention is to provide a precision dispensing pump which has disposable parts exposed to dispensing fluids in order to minimize down time for service.

Another object of the present invention is to provide a precision dispensing pump which has repeatable calibration.

SUMMARY OF THE INVENTION

The invention resides in a precision dispensing pump for dispensing fluids for use in semiconductor packaging and/or semiconductor assembly. The precision dispensing pump comprises a working fluid displacement drive for volumetric displacement of a working fluid, a dispensing reservoir for containment of dispensing fluid and a isolation diaphragm for isolating the working fluid from dispensing fluid in the dispensing reservoir. Volumetric displacement of dispensing fluid in the dispensing reservoir is proportional to volumetric displacement of working fluid in the working fluid displacement drive.

BRIEF DESCRIPTION OF THE DRAWINGS

FIG. 4 is a cross section view of the precision dispensing pump according to FIG. 1 also showing an inlet and outlet valve;

FIG. 5 is the inlet or outlet valve according to FIG. 4 shown in the closed state;

FIG. 6 is the inlet or outlet valve according to FIG. 4 shown in the open state;

FIG. 7 is a cross section view of the precision dispensing pump according to FIG. 1 also showing a switching valve;

FIG. 8 is the switching valve according to FIG. 7 shown in the dispensing state;

FIG. 9 is the switching valve according to FIG. 7 shown in the charging state;

DETAILED DESCRIPTION OF THE EMBODIMENTS

A precision dispensing pump for dispensing a dispensing fluid according to one embodiment of the present invention will now be described in detail with reference to the accompanying drawings.

Figure 1:
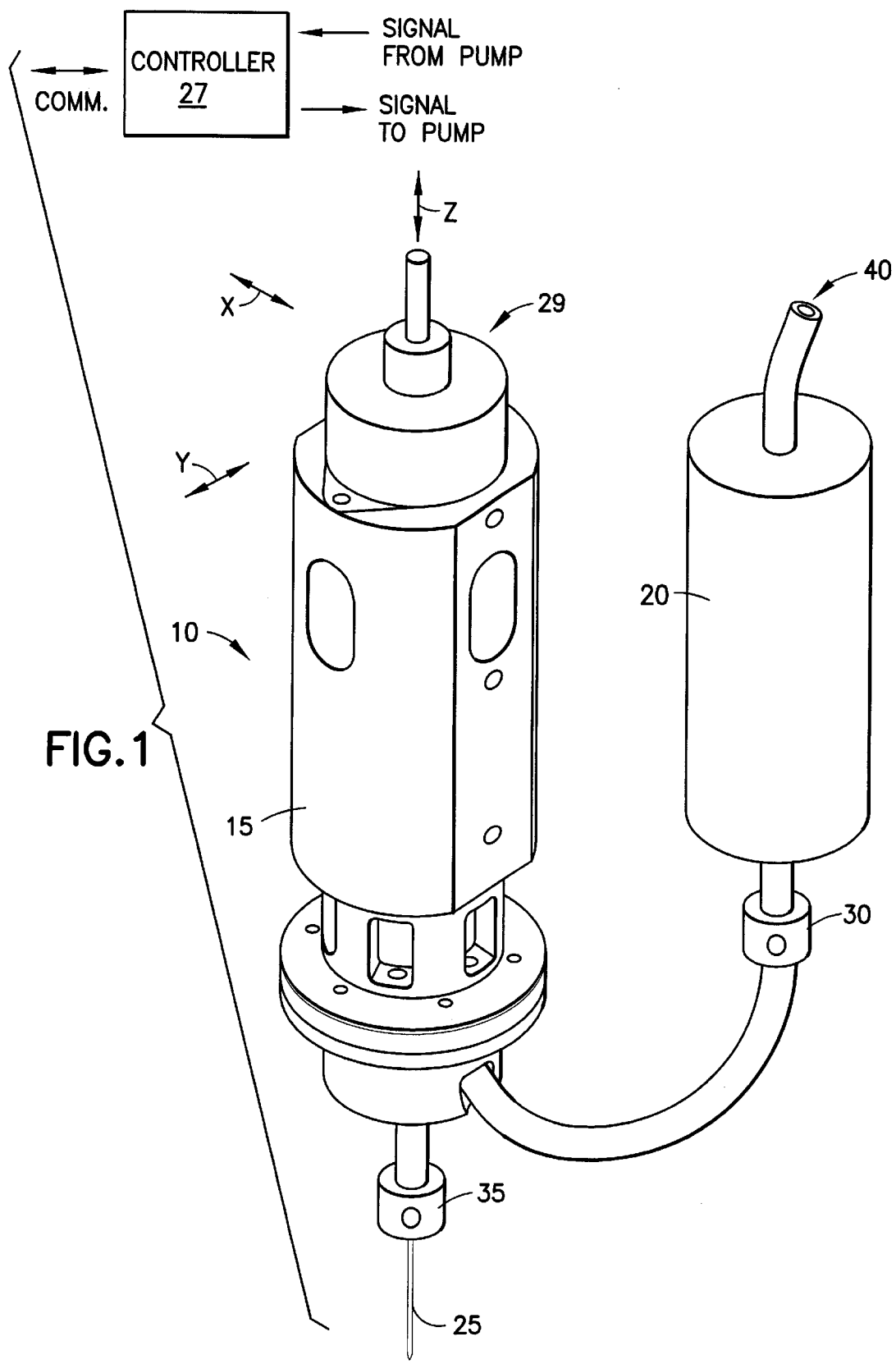
FIG. 1 is a isometric view of a precision dispensing pump according to one embodiment of the present invention.

Referring now to FIG. 1 there is shown is an isometric view of a precision dispensing pump 10. Precision dispensing pump 10 includes a pump body 15, a dispensing fluid container 20, a dispensing needle 25, inlet valve 30 and outlet valve 35. Dispensing fluid such as adhesives or encapsulates are stored in dispensing fluid container 20 which may be a syringe or other suitable container and may or may not be under pressure from pressure source 40. Inlet valve 30 and outlet valve 35 each have two states; either opened or closed. Dispensing fluid enters pump body 15 through inlet valve 30 and exits pump body 15 through outlet valve 35. Dispensing needle 25 is connected to outlet valve 35 and dispensing fluid is ultimately dispensed through dispensing needle 25. Precision dispensing pump 10 is typically mounted to a programmable gantry well known in the art which is capable of movement in directions x, y and z. Pump body 15 alternately draws dispensing fluid from dispensing fluid container 20 and then exhausts dispensing fluid through dispensing needle 25. Controller 27 is used to coordinate the pump motor 29 of pump body 10, inlet valve 30, outlet valve valve 35, pressure source 40 and other pump related functions well known in the art. Controller 27 can be a micro controller, computer, programmable logic controller or other controller well known in the art.

Figure 2:
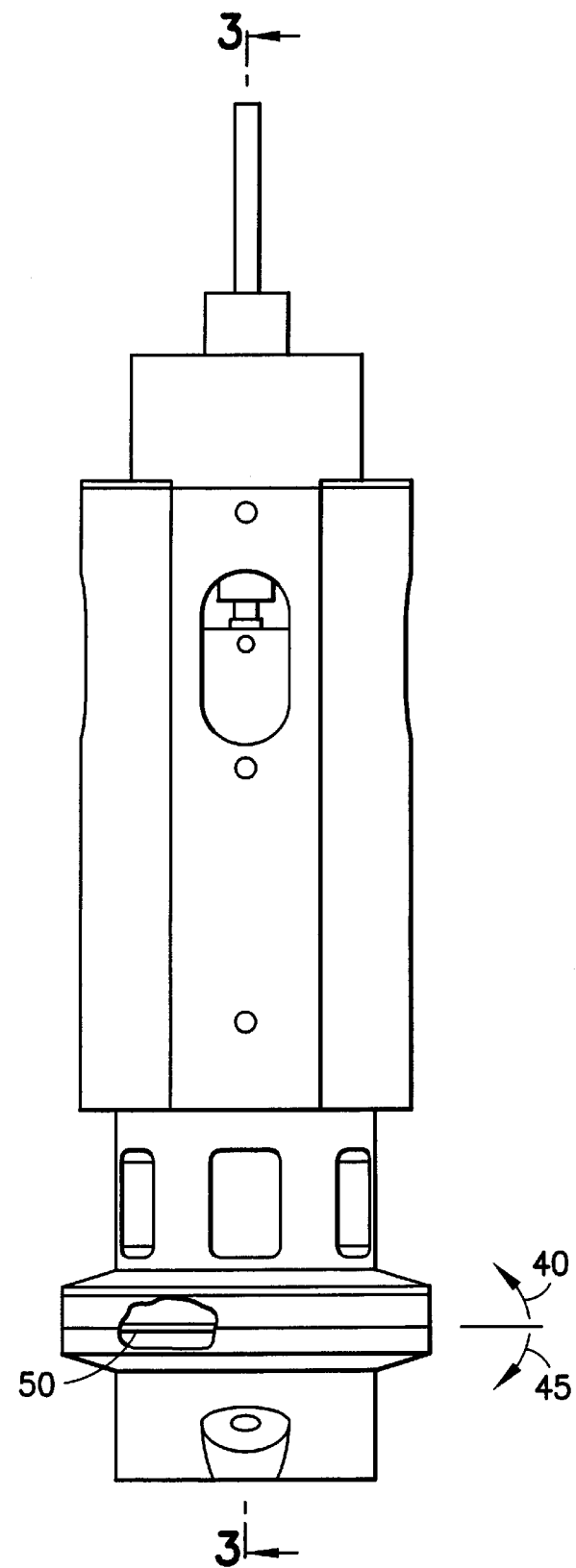
FIG. 2 is a side view of the precision dispensing pump according to FIG. 1.

Referring now to FIG. 2 there is shown a side view of pump body 15 of the precision dispensing pump 10 according to FIG. 1. Pump body 15 includes a working fluid displacement drive 40, a dispensing reservoir 45 and isolation diaphragm 50. Working fluid displacement drive 40 acts as a drive or pump for s the volumetric displacement of a working fluid. The working fluid can be oil, hydraulic fluid, air, any liquid or gas, but is ideally a substantially incompressible fluid. Working fluid displacement drive 40 can be a piston driven, bellows driven, diaphragm driven, or any other type of positive displacement or displacement pump.

Working fluid displacement drive 40 can be driven by a lead screw combined with a stepper motor or servo motor plus encoder which can be dc or ac driven. Alternately, working fluid displacement drive 40 can be driven by a linear motor plus encoder, piezoelectric motor, linear stepper, can be a screw to belt to motor, rotary to linear reciprocating drive, or any other drive known in the art with accurate motion. Working fluid displacement drive 40 can be mounted with precision dispensing pump 10 as shown or can be divided and a portion remotely mounted with the working fluid piped to the remaining portion of precision dispensing pump 10. Dispensing reservoir 45 in combination with isolation diaphragm 50 creates a dispensing volume through which dispensing fluid passes. Dispensing fluid is drawn into dispensing reservoir 45 from dispensing fluid container 20 by expanding the dispensing volume with isolation diaphragm 50. Dispensing fluid is exhausted from dispensing reservoir 45 into dispensing needle 25 by contracting the dispensing volume with isolation diaphragm 50. Isolation diaphragm 50 serves to isolate working fluid from dispensing fluid. Isolation diaphragm 50 is deflected by volumetric displacement of working fluid from working fluid displacement drive 40. Volumetric displacement of working fluid is, as a result, proportional to volumetric displacement of dispensing fluid. Isolation diaphragm 50 can be a single diaphragm or a plurality of diaphragms in contact with each other. Isolation diaphragm 50 can be flat, curved, a bellows shape or other applicable diaphragm shapes and can be made out of metal, plastic or other polymers or materials appropriate for diaphragms. Dispensing reservoir 45 can be made out of metal or plastic or other material that is compatible with dispensing fluid. Dispensing reservoir 45 may be disposable and may have a secondary diaphragm attached to dispensing reservoir 45 which follows a primary diaphragm attached to working fluid displacement drive 40. Dispensing reservoir 45 may be attached to working fluid displacement drive 40 by means of a clamp or quick disconnect clamp collar or other fast release devices known in the art in order to allow simplified cleaning or replacement of parts exposed to dispensing fluid for ease of service with minimum down time for service.

Figure 3:
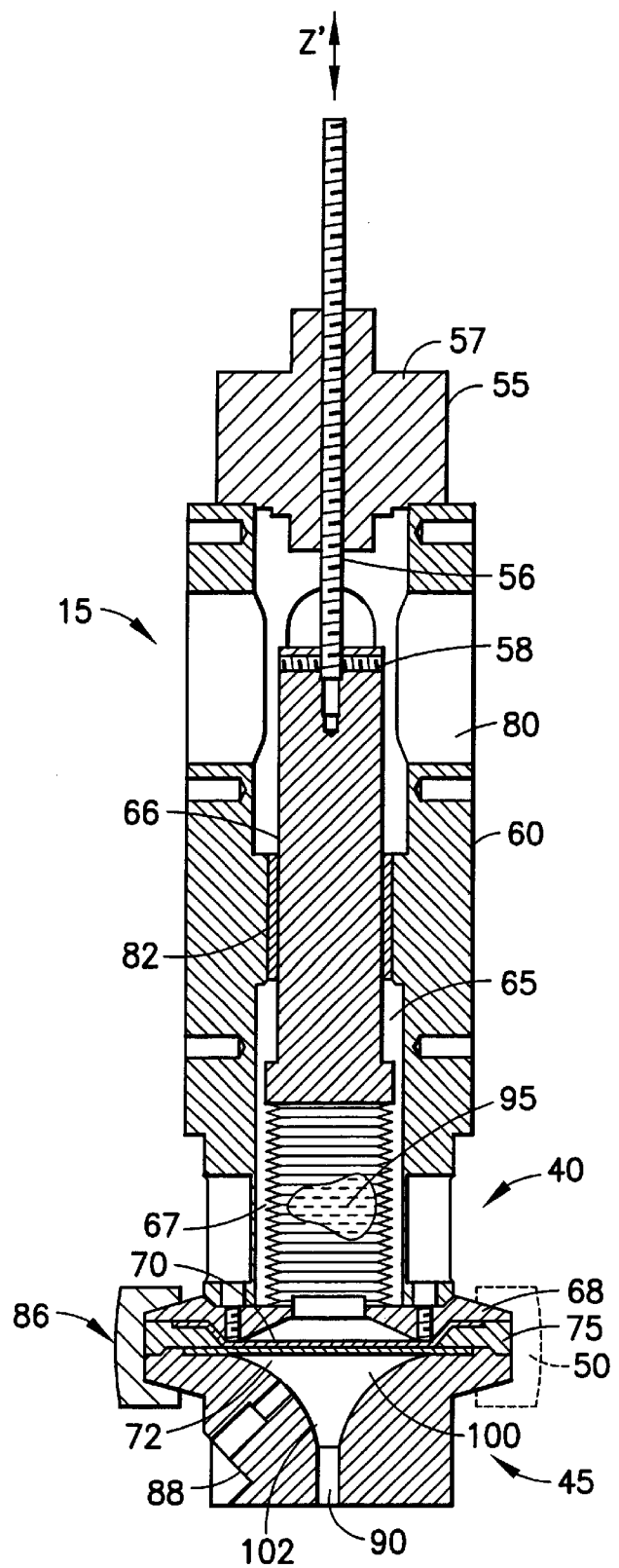
FIG. 3 is a cross section view of the precision dispensing pump according to FIG. 1.

Referring now to FIG. 3 there is shown a cross section view 3—3 of FIG. 2 of pump body 15 of the precision dispensing pump according to FIG. 1. Pump body 15 includes a working fluid displacement drive 40, a dispensing reservoir 45 and isolation diaphragm 50. Working fluid displacement drive 40 includes a motor driven lead screw assembly 55, a housing assembly 60 and bellows assembly 65. Motor driven lead screw 55 includes a lead screw 56 and stepping motor 57. Stepping motor 57 is fastened to housing assembly 60. Lead Screw 56 is fastened to bellows assembly 65 with fasteners 58. When stepping motor 57 is energized, lead screw 56 moves axially in direction z' causing compression or extension of bellows assembly 65. A bellows assembly is preferred construction. As an alternative to bellows assembly 65, a piston may be used. A bellows has advantages over a piston as a bellows does not have moving parts such as dynamic seals which can wear and leak over time and also a bellows can be designed for longer fatigue life beyond that of dynamic seals minimizing or eliminating maintenance. Bellows assembly 65 includes shaft 66, bellows 67 and flange 68. Both flange 68 and shaft 66 are welded to bellows 67. Shaft 66, bellows 67 and flange 68 are typically made out of steel or stainless steel. Shaft 66 is fastened to lead screw 56 with fasteners 58. Flange 68 is fastened to housing assembly 60. Housing assembly 60 includes housing 80 and bushing 82. Bushing 82 is fixed to housing 80 and provides guidance and stability for shaft 66. Isolation diaphragm 50 includes a primary diaphragm 70, a secondary diaphragm 72 and a clamp ring 75. Alternately, isolation diaphragm 50 could include only a single diaphragm. The primary shape of Isolation diaphragm 50 is shown to be flat and round but may alternately be flat and rectangular, concave and round, concave and rectangular or other suitable shape generally for diaphragms known in the art. Clamp ring 75 clamps primary diaphragm 70 to bellows assembly 65. Secondary diaphragm 72 remains in contact with primary diaphragm 70 by a temporary adhesive or thin liquid film. Alternately, secondary diaphragm 72 can simply remain in contact with primary diaphragm 70 due to the pressure applied to or by the dispensing fluid or to or by the working fluid with out need for a temporary adhesive or thin liquid film. Secondary diaphragm 72 can be fastened to dispensing reservoir 45 or alternately be clamped between reservoir 45 and primary diaphragm 70. Dispensing reservoir 45 has an interior surface 102 which is preferably shown generally in the shape of a round vortex. This preferred shape allows the contact area between diaphragm 50 and dispense reservoir 45 to progress and close in on outlet 90 when diaphragm 50 is expanded toward interior surface 102. Alternately, any combination of shapes may be applied to diaphragm 50 and interior surface 102 which allows the contact area between diaphragm 50 and dispense reservoir 45 to progress and close in on outlet 90 when diaphragm 50 is expanded toward interior surface 102. Alternately, dispensing reservoir 45 can have an interior surface generally in a concave shape and also can either be round, rectangular or other suitable shape. Dispensing reservoir 45 has inlet 88 and outlet 90. Alternately, outlet 90 may operate as both an inlet and an outlet to dispense reservoir 45 thus eliminating inlet 88. Inlet 88 is preferably located in close proximity to the interface between dispense reservoir 45 and diaphragm 50 when diaphragm 50 comprises a single diaphragm. Inlet 88 is preferably located in close proximity to the interface between dispense reservoir 45 and secondary diaphragm 72 when diaphragm 50 comprises a primary diaphragm 70 and secondary diaphragm 72. When inlet 88 is located as preferred, the filling and gas purging cycle is minimized as dispensing fluid enters dispensing volume 100 at its outer edge when diaphragm 50 is contracted away from interior surface 102 and exits dispensing volume 100 at outlet 90 when the contact area between diaphragm 50 and dispense reservoir 45 progresses and closes in on outlet 90 when diaphragm 50 is expanded toward interior surface 102. When inlet 88 is located as preferred, any gas remaining in dispensing volume 100 during a purge, fill or dispense cycle will be minimized as it can not re-enter dispensing volume 100 such as in the case where outlet 90 operates as both an inlet and an outlet to dispense reservoir 45 thus eliminating inlet 88. Dispensing reservoir 45 is clamped to bellows assembly 65 using pump clamp 86. Pump clamp 86 can be a clamp or quick disconnect clamp collar such as a KF type vacuum clamp or other fast release clamping devices known in the art in order to allow simplified cleaning or replacement for ease of service with minimum down time for service. Working fluid is contained in interior region 95 of the bellows assembly 65 and isolation diaphragm 50. Dispensing fluid is contained and dispensed via dispensing volume 100 of dispensing reservoir 45 and isolation diaphragm 50. Removal of pump clamp 86 allows quick removal and replacement or cleaning of dispensing reservoir 45 and a portion of isolation diaphragm 50 if applicable.

Referring now to FIG. 4 is a cross section view of the precision dispensing pump according to FIG. 3 also showing inlet valve 104 and outlet valve 108. Inlet valve 104 has a supply port 112 and a inlet port 110. Outlet valve 108 has an outlet port 114 and a dispense port 116. Supply port 112 is connected to dispensing fluid container 20. Inlet port 110 is connected to inlet 88 of dispense reservoir 45. Outlet port 114 is connected to outlet 90 of dispense reservoir 45. Dispense port 116 is connected to dispensing needle 25.

Referring now to FIG. 5 is inlet valve 104 or outlet valve 108 according to FIG. 4 shown in the closed state where dispensing fluid will not flow.

Referring now to FIG. 6 is inlet valve 104 or outlet valve 108 according to FIG. 4 shown in the open state where dispensing fluid may flow.

Referring now to FIG. 7 is a cross section view of the precision dispensing pump according to FIG. 3 also showing switching valve 120. Switching valve 120 has a supply port 122, a reservoir port 126 and dispense port 124. Supply port 122 is connected to dispensing fluid container 20. Reservoir port 126 is connected to port 130 of dispense reservoir 45. Dispense port 124 is connected to dispensing needle 25.

Referring now to FIG. 8 is switching valve 120 according to FIG. 7 shown in the dispensing position where dispensing fluid may flow from dispense reservoir 45 to dispensing needle 25.

Referring now to FIG. 9 is switching valve 120 according to FIG. 7 shown in the charging position where dispensing fluid may flow from dispensing fluid container 20 to dispense reservoir 45. Switching valve 120 may also be placed in an intermediate position between the charging position of FIG. 9 and the dispensing position of FIG. 8 in order to effectuate a stoppage of flow.

Figure 10:
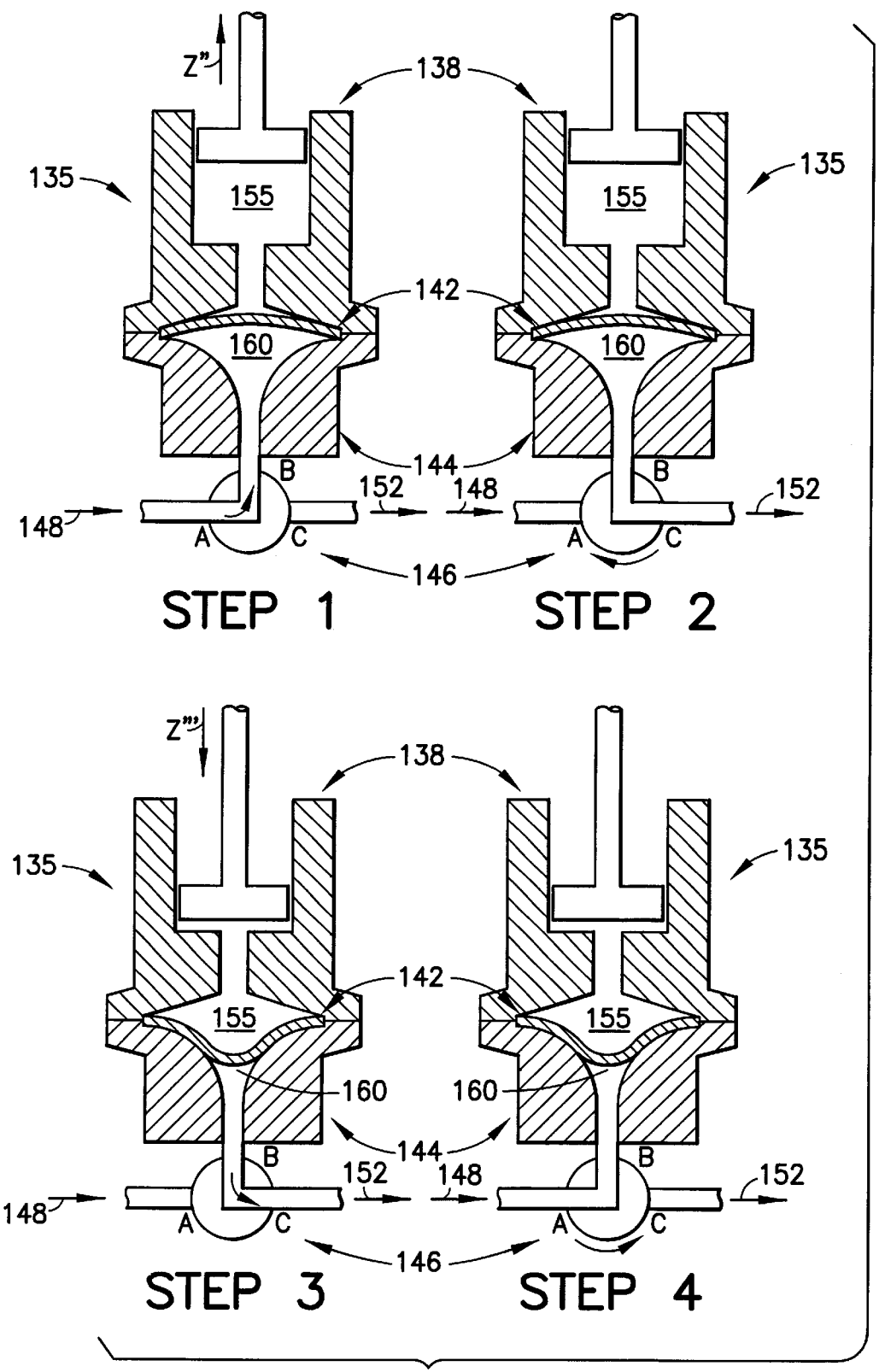
FIG. 10 is a diagram showing the dispensing sequence of a precision dispensing pump according to one embodiment of the present invention.

Referring now to FIG. 10 is a diagram showing the dispensing sequence of a precision dispensing pump according to one embodiment of the present invention. Referring to steps one through four of FIG. 10, precision dispensing pump 135 includes piston 138, isolation diaphragm 142, dispense reservoir 144, and switching valve 146. Switching valve 146 has ports A, B and C. Port A is connected to dispensing fluid container 148, port B is connected to dispense reservoir 144 and port C is connected to dispensing needle 152. When switching valve 146 is in a charging position, port A communicates with port B and port C is closed. When switching valve 146 is in a dispensing position, port B communicates with port C and port A is closed. Working fluid 155 is isolated from dispensing fluid 160 by isolation diaphragm 142. In step 1, dispensing fluid 160 is drawn from dispensing fluid container 148 into dispense reservoir 144 by drawing piston 138 in direction z". In step 2, switching valve 146 is changed from the charging position state to the dispensing position state. In step 3, dispensing fluid is exhausted from dispense reservoir 144 to dispensing needle 152 by drawing piston 138 in direction z'". In step 4, switching valve 146 is changed from the dispensing position state to the charging position state. Steps 1 through 4 are then repeated to continue the dispense cycle until dispensing fluid has been exhausted. Alternately, the dispense sequence recited may be accomplished using an inlet valve and outlet valve as previously described instead of a switching valve to achieve the same functional result. For the charging state, this may be achieved by having the inlet valve open and the outlet valve closed. For the dispensing state this may be achieved by having the inlet valve closed and the outlet valve open. The intermediate position of the switching valve where none of ports A,B or C communicate with each other corresponds to the state where both the inlet valve and outlet valve are closed in the alternate embodiment.

While the present invention has been particularly described with respect to certain elements in its preferred embodiments, it will be understood that the invention is not limited to those particular methods and/or apparatus' described in the preferred embodiments, the process steps, the sequence or the final structures depicted in the drawings. On the contrary, it is intended to cover all alternatives, modifications, and equivalents as may be included within the the spirit and scope of the invention defined by the appended claims. In addition, other methods and/or devices may be employed in the apparatus of the instant invention.

Figure 11:
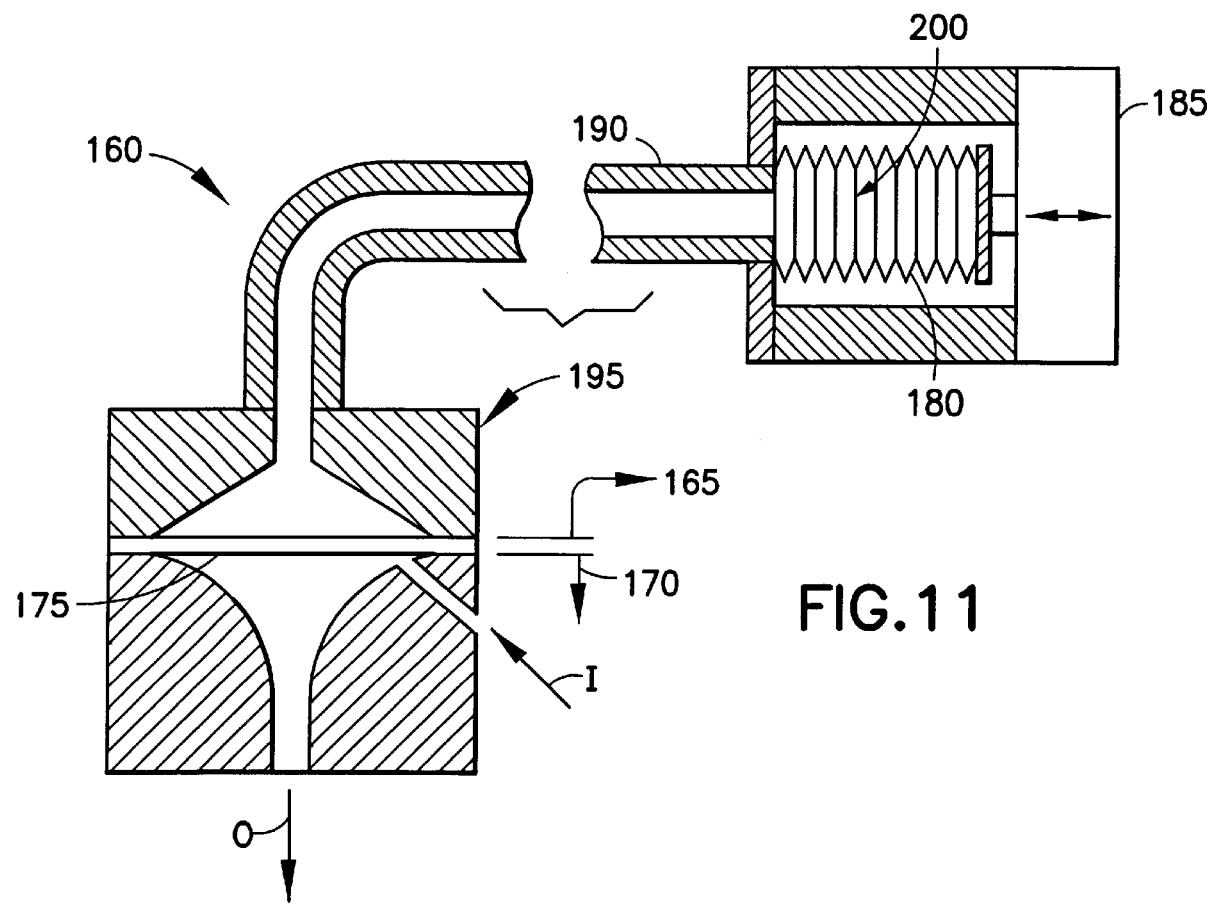
FIG. 11 is a diagram showing a precision dispensing pump with a portion of the working fluid displacement drive remotely operable.

Referring to FIG. 11 is a diagram showing a precision dispensing pump with a portion of the working fluid displacement drive remotely operable. Pump 160 includes a working fluid displacement drive 165, a dispensing reservoir 170 and isolation diaphragm 175. Working fluid displacement drive 165 includes bellows assembly 180, motor driven lead screw 185, tubing 190 and interface 195. Working fluid 200 is pumped between bellows assembly 200 and interface 195 via tubing 190.

Figure 12:
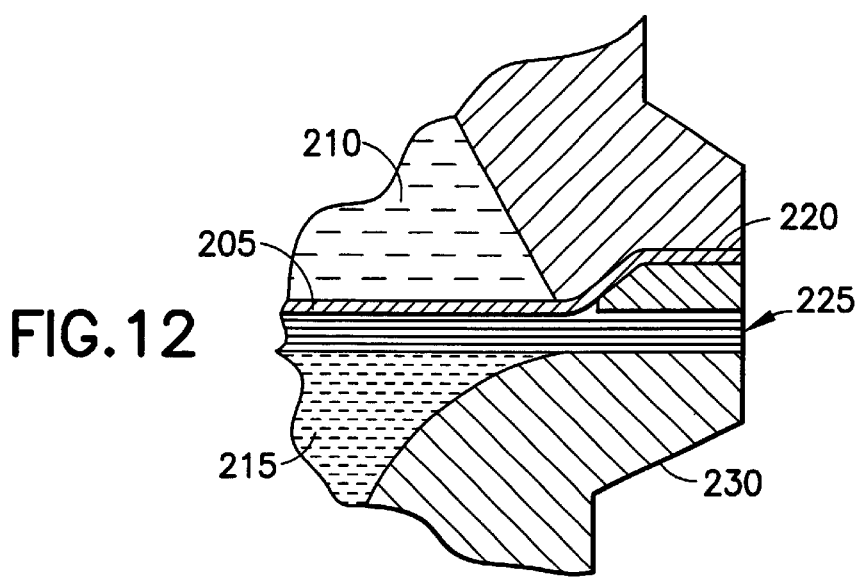
FIG. 12 is a cross section view of a portion of the isolation diaphragm of one embodiment of the present invention.

Referring now to FIG. 12 is a cross section view of a portion of the isolation diaphragm of one alternative embodiment of the present invention. Isolation diaphragm 205 isolates working fluid 210 from dispensing fluid 215. Isolation diaphragm 205 comprises primary diaphragm 220 and secondary diaphragm(s) 225. Secondary diaphragm(s) 225 are adhered adjacent to primary diaphragm 220 temporarily and may be a plurality of thin stacked membranes which are compatible with dispensing fluid 215. Dispensing reservoir 230 is removable for cleaning or disposal after use for dispensing. To clean and remove dispensing to fluid from Isolation diaphragm 205, one of the thin membranes of secondary diaphragm(s) 225 is peeled away and disposed.

What is claimed is:

1. A precision dispensing pump for dispensing a dispensing fluid, comprising:
   a working fluid displacement drive having a bellows for containment of a working fluid;
   the working fluid displacement drive for volumetric displacement of said working fluid;
   a dispensing reservoir for containment of dispensing fluid;
   a isolation diaphragm for isolating said working fluid in said working fluid displacement drive from dispensing fluid in said dispensing reservoir;
   wherein volumetric displacement of dispensing fluid in said dispensing reservoir is proportional to volumetric displacement of said working fluid in said working fluid displacement drive.

2. The precision dispensing pump according to claim 1 wherein said working fluid displacement drive further comprises:
   a linear drive coupled to said bellows;
   wherein linear displacement of said linear drive effects volumetric displacement of said working fluid.

3. The precision dispensing pump according to claim 2 wherein said linear drive comprises:
   a motor driven lead screw; and
   a bushing guided housing for linear constraint of said bellows.

4. The precision dispensing pump according to claim 2 wherein said linear drive comprises a motor driven lead screw.

5. The precision dispensing pump according to claim 1 further comprising:
   a inlet valve having a supply port and a inlet port;

said supply port connected to a dispensing fluid container;
said inlet port connected to said dispensing reservoir;
a outlet valve having a outlet port and a dispense port;
said outlet port connected to said dispensing reservoir.

6. The precision dispensing pump according to claim 5 wherein said working fluid displacement drive further comprises:
   a linear drive coupled to said bellows;
   wherein linear displacement of said linear drive effects volumetric displacement of said working fluid.

7. The precision dispensing pump according to claim 6 wherein said linear drive comprises:
   a motor driven lead screw; and
   a bushing guided housing for linear constraint of said bellows.

8. The precision dispensing pump according to claim 1 further comprising:
   a switching valve having a supply port, a reservoir port and a dispense port;
   said supply port connected to a dispensing fluid container;
   said reservoir port connected to said dispensing reservoir;
   said switching valve having a charging position and a dispensing position
   wherein said supply port is connected to said reservoir port when said switching valve is in said charging position;
   wherein said reservoir port is connected to said dispense port when said switching valve is in said dispensing position.

9. The precision dispensing pump according to claim 8 wherein said working fluid displacement drive further comprises:
   a linear drive coupled to said bellows;
   wherein linear displacement of said linear drive effects volumetric displacement of said working fluid.

10. The precision dispensing pump according to claim 9 wherein said linear drive comprises:
    a motor driven lead screw; and
    a bushing guided housing for linear constraint of said bellows.

11. A precision dispensing pump for dispensing a dispensing fluid, comprising:
    a working fluid displacement drive for volumetric displacement of a working fluid
    a dispensing reservoir for containment of dispensing fluid;
    a isolation diaphragm for isolating said working fluid in said working fluid displacement drive from dispensing fluid in said dispensing reservoir;
    said isolation diaphragm having a primary diaphragm and a secondary diaphragm;
    said primary diaphragm having a primary working side and a primary interfacing side;
    said primary working side sealed to said working fluid displacement drive;
    said secondary diaphragm having a secondary interfacing side and a secondary dispensing side;
    said secondary dispensing side sealed to said dispensing reservoir;
    said primary interfacing side mating with said secondary interfacing side;
    wherein volumetric displacement of dispensing fluid in said dispensing reservoir is proportional to volumetric displacement of working fluid in said working fluid displacement drive.

12. The precision dispensing pump according to claim 11 wherein said working fluid displacement drive comprises:
    a bellows for containment of said working fluid;
    a linear drive coupled to said bellows;
    wherein linear displacement of said linear drive effects volumetric displacement of said working fluid.

13. The precision dispensing pump according to claim 12 wherein said linear drive comprises:
    a motor driven lead screw; and
    a bushing guided housing for linear constraint of said bellows.

14. The precision dispensing pump according to claim 11 wherein said working fluid displacement drive comprises:
    a piston for containment of said working fluid;
    a linear drive coupled to said piston
    wherein linear displacement of said linear drive effects volumetric displacement of said working fluid.

15. The precision dispensing pump according to claim 14 wherein said linear drive comprises a motor driven lead screw.

16. The precision dispensing pump according to claim 11 further comprising:
    a inlet valve having a supply port and a inlet port;
    said supply port connected to a dispensing fluid container;
    said inlet port connected to said dispensing reservoir;
    a outlet valve having a outlet port and a dispense port;
    said outlet port connected to said dispensing reservoir.

17. The precision dispensing pump according to claim 16 wherein said working fluid displacement drive comprises:
    a piston for containment of said working fluid;
    a linear drive coupled to said piston;
    wherein linear displacement of said linear drive effects volumetric displacement of said working fluid.

18. The precision dispensing pump according to claim 17 wherein said linear drive comprises a motor driven lead screw.

19. The precision dispensing pump according to claim 16 wherein said working fluid displacement drive comprises:
    a bellows for containment of said working fluid;
    a linear drive coupled to said bellows;
    wherein linear displacement of said linear drive effects volumetric displacement of said working fluid.

20. The precision dispensing pump according to claim 19 wherein said linear drive comprises:
    a motor driven lead screw; and
    a bushing guided housing for linear constraint of said bellows.

21. The precision dispensing pump according to claim 11 further comprising:
    a switching valve having a supply port, a reservoir port and a dispense port;
    said supply port connected to a dispensing fluid container;
    said reservoir port connected to said dispensing reservoir;
    said switching valve having a charging position and a dispensing position;
    wherein said supply port is connected to said reservoir port when said switching valve is in said charging position;
    wherein said reservoir port is connected to said dispense port when said switching valve is in said dispensing position.

22. The precision dispensing pump according to claim 21 wherein said working fluid displacement drive comprises:
    a bellows for containment of said working fluid;
    a linear drive coupled to said bellows;
    wherein linear displacement of said linear drive effects volumetric displacement of said working fluid.

23. The precision dispensing pump according to claim 22 wherein said linear drive comprises:
   a motor driven lead screw; and
   a bushing guided housing for linear constraint of said bellows.

24. The precision dispensing pump according to claim 21 wherein said working fluid displacement drive comprises:
   a piston for containment of said working fluid;
   a linear drive coupled to said piston;
wherein linear displacement of said linear drive effects volumetric displacement of said working fluid.

25. The precision dispensing pump according to claim 24 wherein said linear drive comprises a motor driven lead screw.

26. A method of dispensing a dispensing fluid, comprising the steps of:
   providing a bellows for volumetric displacement of a working fluid;
   providing a dispensing reservoir for containment of dispensing fluid in a dispensing volume;
   providing a isolation diaphragm for isolating said working fluid in said bellows from dispensing fluid in said dispensing reservoir;
   connecting said dispensing volume to a dispensing fluid container;
   drawing dispensing fluid from said dispensing fluid container into said dispensing volume by expanding said dispensing volume;
   isolating said dispensing volume from said dispensing fluid container;
   connecting said dispensing volume to a dispensing outlet;
   exhausting dispensing fluid from said dispensing volume through said dispensing outlet by contracting said dispensing volume.

* * * * *